US012768968B2

(12) United States Patent
Horiuchi et al.

(10) Patent No.: US 12,768,968 B2
(45) Date of Patent: Oct. 20, 2026

(54) DISTANCE MEASUREMENT DEVICE, RADIOGRAPHY SYSTEM, OPERATION METHOD OF DISTANCE MEASUREMENT DEVICE, AND OPERATION PROGRAM

(71) Applicant: FUJIFILM CORPORATION, Tokyo (JP)

(72) Inventors: Hisatsugu Horiuchi, Kanagawa (JP); Tetsuya Tsuji, Kanagawa (JP); Kazuhiro Makino, Kanagawa (JP); Naoyuki Nishino, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 155 days.

(21) Appl. No.: 18/824,920

(22) Filed: Sep. 5, 2024

(65) Prior Publication Data

US 2025/0110063 A1 Apr. 3, 2025

(30) Foreign Application Priority Data

Sep. 28, 2023 (JP) ................................ 2023-168776

(51) Int. Cl.
*A61B 6/00* (2024.01)
*A61B 6/58* (2024.01)
(Continued)

(52) U.S. Cl.
CPC ............ *G01S 7/497* (2013.01); *A61B 6/4452* (2013.01); *A61B 6/4464* (2013.01); *A61B 6/545* (2013.01);
(Continued)

(58) Field of Classification Search
None
See application file for complete search history.

(56) References Cited

U.S. PATENT DOCUMENTS 11,536,814 B2 * 12/2022 Nakamura ............ G01S 17/894
11,690,588 B2 * 7/2023 Kitano .................. A61B 6/488 378/62
(Continued)

FOREIGN PATENT DOCUMENTS

CN 209916029 U * 1/2020
CN 113876341 A * 1/2022 ............ A61B 6/589
(Continued)

*Primary Examiner* — Thomas R Artman
(74) *Attorney, Agent, or Firm* — SOLARIS Intellectual Property Group, PLLC

(57) ABSTRACT

The distance measurement device includes a ToF type distance measurement camera that measures a distance to a measurement object and a distance to a reference object of which the distance is known, and a processor. The processor calculates a correction coefficient on the basis of a first measurement value that is a measurement value of a distance from the distance measurement camera to the reference object obtained by the distance measurement camera and a known distance from the distance measurement camera to the reference object, and corrects a second measurement value that is a measurement value of a distance from the distance measurement camera to the measurement object obtained by the distance measurement camera or a calculation value calculated using the second measurement value.

12 Claims, 12 Drawing Sheets

(51) Int. Cl.

| | |
|---|---|
| ***G01S 7/497*** | (2006.01) |
| ***G01S 17/36*** | (2006.01) |
| ***G01S 17/93*** | (2020.01) |

(52) U.S. Cl.

CPC .............. *A61B 6/547* (2013.01); *A61B 6/582* (2013.01); *A61B 6/588* (2013.01); *A61B 6/589* (2013.01); *G01S 17/36* (2013.01); *G01S 17/93* (2013.01); *A61B 2560/0223* (2013.01)

(56) References Cited

U.S. PATENT DOCUMENTS

| | | | | | |
|---|---|---|---|---|---|
| 12,042,322 | B2 * | 7/2024 | Kitano | ................. | A61B 6/5258 |
| 12,277,720 | B2 * | 4/2025 | Oda | .......................... | G06T 7/70 |
| 12,496,028 | B2 * | 12/2025 | Taki | ....................... | A61B 6/482 |
| 12,569,215 | B2 * | 3/2026 | Horiuchi | ................ | A61B 6/548 |
| 2020/0018836 | A1 * | 1/2020 | Nakamura | .............. | G01S 17/08 |
| 2021/0378617 | A1 * | 12/2021 | Kitano | ................. | A61B 6/5258 |
| 2021/0378622 | A1 | 12/2021 | Kitano | | |
| 2023/0005168 | A1 * | 1/2023 | Oda | .......................... | G06T 7/60 |
| 2023/0293134 | A1 * | 9/2023 | Horiuchi | ................ | A61B 6/548 378/62 |
| 2023/0404510 | A1 * | 12/2023 | Taki | ....................... | A61B 6/482 |
| 2024/0358345 | A1 * | 10/2024 | Cheng | .................... | A61B 6/588 |
| 2025/0110063 | A1 * | 4/2025 | Horiuchi | ................. | G01S 7/497 |

FOREIGN PATENT DOCUMENTS

| | | | | | |
|---|---|---|---|---|---|
| JP | 2021-191389 | A | | 12/2021 | |
| TW | 202443109 | A | * | 11/2024 | ............. G16H 30/20 |

* cited by examiner

DISTANCE MEASUREMENT DEVICE, RADIOGRAPHY SYSTEM, OPERATION METHOD OF DISTANCE MEASUREMENT DEVICE, AND OPERATION PROGRAM

CROSS-REFERENCE TO RELATED APPLICATIONS

The present application claims priority under 35 U.S.C. § 119 to Japanese Patent Application No. 2023-168776, filed on Sep. 28, 2023. The above application is hereby expressly incorporated by reference, in its entirety, into the present application.

BACKGROUND

1. Technical Field

The technology of the present disclosure relates to a distance measurement device, a radiography system, an operation method of the distance measurement device, and an operation program.

2. Description of the Related Art

In radiography, it is desirable to appropriately set imaging conditions according to a body thickness of a subject such as a patient. The imaging conditions include a tube voltage and a tube current time product of a radiation source. It is desirable to set the imaging conditions such that radiography is performed with an appropriate radiation dose according to the body thickness of the subject.

Since the body thickness varies depending on the subject to be a target of the radiography, it is necessary to accurately measure the body thickness in order to appropriately set the imaging conditions. JP2021-191389A discloses that a body thickness is obtained using a measurement value obtained by a time-of-flight (ToF) type distance measurement camera. The ToF type distance measurement camera is also used in a field other than the medical field.

SUMMARY

The ToF type distance measurement camera has an advantage that measurement can be performed with high accuracy, but has a problem of so-called temperature drift in which a measurement value is changed due to an increase in a temperature inside a device after power supply is turned on. It is also conceivable to measure the temperature inside the device and perform temperature correction, but a sensor used in the ToF type distance measurement camera is small, and it is difficult to measure the temperature of the sensor itself. In addition, it is also conceivable to measure an ambient temperature of the sensor instead of the temperature of the sensor itself and perform temperature correction, but it is difficult to perform measurement with high accuracy because the ambient temperature is different from the temperature of the sensor itself. Furthermore, it is also conceivable to perform the measurement after the temperature inside the device is stabilized, but it takes a certain period of time for the temperature to stabilize, and thus the measurement cannot be performed quickly.

An object of the technology of the present disclosure is to provide a distance measurement device, a radiography system, an operation method of the distance measurement device, and an operation program that enable measurement to be performed quickly with high accuracy.

In order to achieve the object, a distance measurement device according to an aspect of the present disclosure includes a ToF type distance measurement camera that measures a distance to a measurement object and a distance to a reference object of which the distance is known; and a processor, in which the processor calculates a correction coefficient on the basis of a first measurement value that is a measurement value of a distance from the distance measurement camera to the reference object obtained by the distance measurement camera and a known distance from the distance measurement camera to the reference object, and corrects a second measurement value that is a measurement value of a distance from the distance measurement camera to the measurement object obtained by the distance measurement camera or a calculation value calculated using the second measurement value.

It is preferable that a plurality of reference objects are provided, and the processor calculates the correction coefficient on the basis of an average value of a plurality of first measurement values that are measurement values of distances from the distance measurement camera to the plurality of reference objects obtained by the distance measurement camera, and known distances from the distance measurement camera to the plurality of reference objects.

It is preferable that the first measurement value is an average value of a plurality of measurement values obtained by measuring a distance from the distance measurement camera to the reference object a plurality of times by using the distance measurement camera.

It is preferable that the calculation value is a difference value between the first measurement value and the second measurement value.

It is preferable that the processor sets a value obtained by dividing the first measurement value by the known distance as the correction coefficient, and corrects the second measurement value or the calculation value by multiplying the second measurement value or the calculation value by the correction coefficient.

It is preferable that the processor updates the correction coefficient by acquiring the first measurement value at a constant time interval and calculating the correction coefficient.

It is preferable that the processor updates the correction coefficient by acquiring the first measurement value and calculating the correction coefficient at shorter intervals as an elapsed time from power supply turn-on of the distance measurement camera is shorter.

It is preferable that the distance measurement device further includes a detection sensor that detects a position of the distance measurement camera with respect to the reference object, and the processor obtains the known distance by using a detection value detected by the detection sensor.

It is preferable that the reference object is an imaging stand, the measurement object is a subject disposed with respect to the imaging stand, the calculation value is a difference value between the first measurement value and the second measurement value, and the processor calculates a body thickness of the subject by multiplying the calculation value by the correction coefficient.

A radiography system according to another aspect of the present disclosure includes the distance measurement device described above; a radiation source that emits radiation toward the imaging stand; and a radiation image detector that is provided on the imaging stand and detects the radiation to generate a radiation image.

It is preferable that the distance measurement camera is attached to the radiation source.

An operation method of a distance measurement device according to another aspect of the present disclosure is an operation method of a distance measurement device provided with a ToF type distance measurement camera that measures a distance to a measurement object and a distance to a reference object of which the distance is known, in which a processor executes processing including calculating a correction coefficient on the basis of a first measurement value that is a measurement value of a distance from the distance measurement camera to the reference object obtained by the distance measurement camera and a known distance from the distance measurement camera to the reference object, and correcting a second measurement value that is a measurement value of a distance from the distance measurement camera to the measurement object obtained by the distance measurement camera or a calculation value calculated using the second measurement value.

An operation program according to another aspect of the present disclosure is an operation program for operating a distance measurement device including a ToF type distance measurement camera that measures a distance to a measurement object and a distance to a reference object of which the distance is known, the operation program causing a processor to execute processing including calculating a correction coefficient on the basis of a first measurement value that is a measurement value of a distance from the distance measurement camera to the reference object obtained by the distance measurement camera and a known distance from the distance measurement camera to the reference object; and correcting a second measurement value that is a measurement value of a distance from the distance measurement camera to the measurement object obtained by the distance measurement camera or a calculation value calculated using the second measurement value.

According to the technology of the present disclosure, it is possible to provide a distance measurement device, a radiography system, an operation method of the distance measurement device, and an operation program that enable measurement to be performed quickly with high accuracy.

BRIEF DESCRIPTION OF THE DRAWINGS

Exemplary embodiments according to the technique of the present disclosure will be described in detail based on the following figures, wherein.

DETAILED DESCRIPTION

An example of embodiments according to the technology of the present disclosure will be described with reference to the accompanying drawings.

First Embodiment

Figure 1:
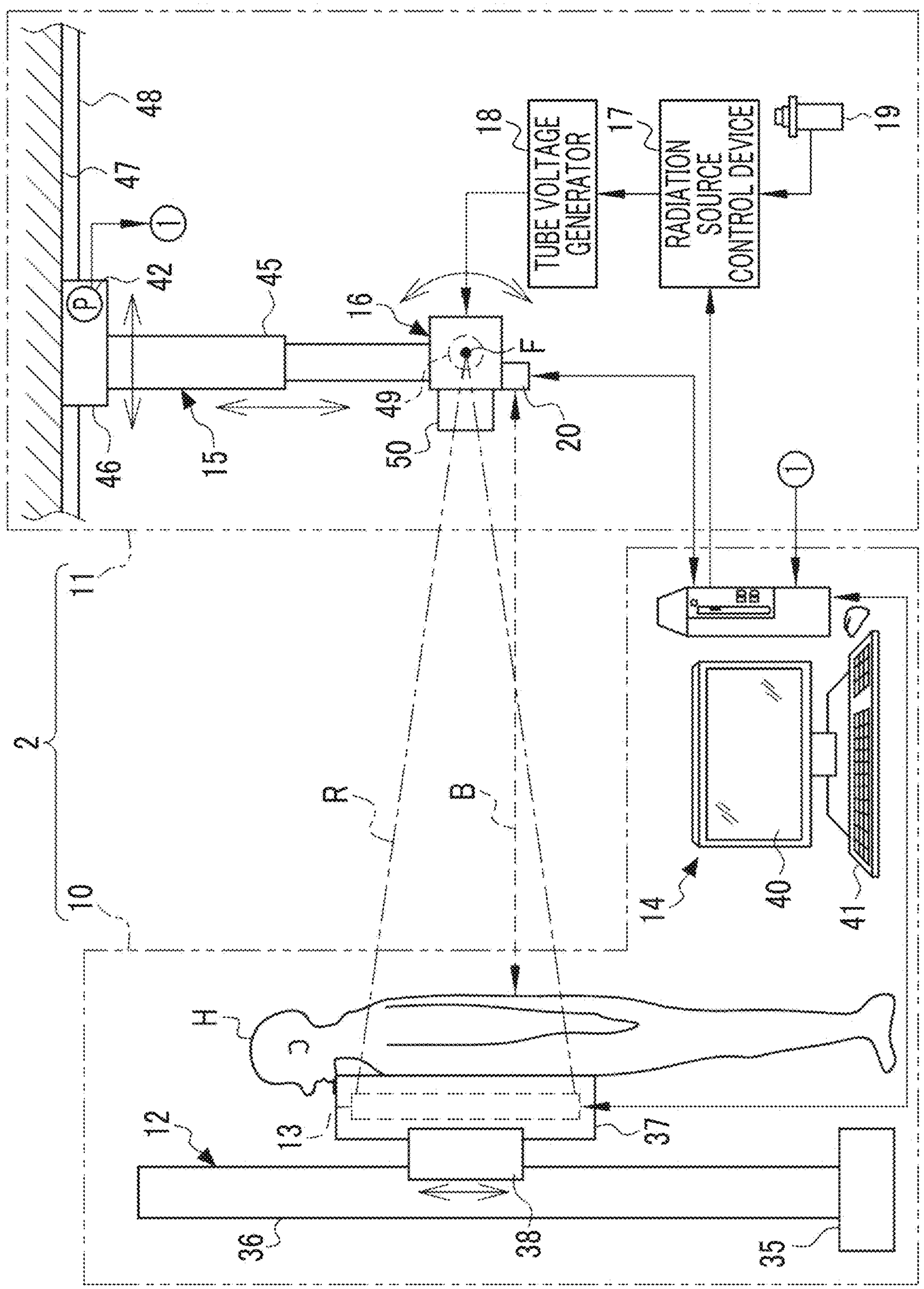
FIG. 1 is a diagram schematically illustrating an example of a configuration of a radiography system.

FIG. 1 is a diagram schematically illustrating an example of a configuration of a radiography system 2. The radiography system 2 is a system that performs radiography of a subject H using radiation (for example, X-rays) R, and includes a radiography device 10 and a radiation generation device 11. The radiography device 10 includes an upright imaging stand 12, an electronic cassette 13, and a console 14. The radiation generation device 11 includes a radiation source suspension device 15, a radiation source 16, a radiation source control device 17, a tube voltage generator 18, and an irradiation switch 19. A ToF type distance measurement camera 20 is attached to the radiation source 16.

The upright imaging stand 12 is an imaging stand for performing radiography of the subject H in an upright posture. The upright imaging stand 12 has a pedestal 35 that is installed on a floor of a radiography room, a support 36 that extends in a height direction from the pedestal 35, and a holder 37 that holds the electronic cassette 13 therein. The holder 37 is connected to the support 36 via a connecting portion 38. The holder 37 is raised or lowered along the support 36 by a motor or the like in accordance with an imaging part. The upright imaging stand 12 is an example of an "imaging stand" according to the technology of the present disclosure.

The electronic cassette 13 is a portable radiation image detector that detects the radiation R transmitted through the subject H to generate a radiation image. The electronic cassette 13 is connected to the console 14 to be communicable in a wired or wireless manner. The electronic cassette 13 is used by being accommodated in the holder 37 of the upright imaging stand 12.

The electronic cassette 13 has a detection panel in which a plurality of pixels for accumulating electric charge depending on the radiation R are arranged in a two-dimensional matrix. The detection panel is also called a flat panel detector (FPD).

The console 14 is, for example, a personal computer. The console 14 includes a display 40 that displays various screens, and an input device 41 that receives an operation instruction of an operator. The input device 41 includes a keyboard, a mouse, and the like. The console 14 transmits various signals to the electronic cassette 13. In addition, the console 14 receives a radiation image 66 from the electronic cassette 13. The console 14 displays the radiation image 66 on the display 40.

The radiation source suspension device 15 includes an arm 45 and a carriage 46. The radiation source 16 is attached to a distal end of the arm 45. A base end of the arm 45 is attached to the carriage 46. The arm 45 can expand and contract along a vertical direction by a motor or the like. The arm 45 is made to expand and contract in the vertical direction, and thereby a height position of the radiation source 16 can be changed conforming to the imaging part. In addition, the radiation source 16 is rotated around an axis perpendicular to the paper plane with respect to the arm 45 by a motor or the like to adjust an incidence angle of the radiation R on the subject H.

The carriage 46 is connected to a rail 48 laid on a ceiling 47 of a radiography room 25. The rail 48 is parallel to a normal line of a detection surface of the electronic cassette 13 accommodated in the holder 37 with respect to the radiation R. The carriage 46 and the radiation source 16 can be moved in parallel along the rail 48 by a motor or the like. By moving the radiation source 16 along the rail 48, a source-to-image receptor distance (SID), which is a distance from a focal point F of the radiation R to the detection surface for the radiation R of the electronic cassette 13 is changed. The position of the carriage 46 with respect to the rail 48 is detected by, for example, a detection sensor 42 such as a potentiometer or a linear encoder. A detection value of the position detected by the detection sensor 42 is a value corresponding to the SID, and is output to the console 14.

The radiation source 16 has a radiation tube 49 and an irradiation field limiter 50. The radiation tube 49 is provided with a filament, a target, a grid electrode, and the like (all are not illustrated). A voltage is applied between the filament which is a cathode, and the target which is an anode. The voltage to be applied between the filament and the target is referred to as a tube voltage. The filament releases thermal electrons according to the applied tube voltage toward the target. The target radiates the radiation R with collision of the thermal electrons from the filament. The grid electrode is disposed between the filament and the target. The grid electrode changes a flow rate of the thermal electrons from the filament toward the target according to the applied voltage. The flow rate of the thermal electrons from the filament toward the target is referred to as a tube current.

The irradiation field limiter 50 is also called a collimator, and limits an irradiation field of the radiation R emitted from the radiation tube 49. The irradiation field limiter 50 has, for example, a configuration in which four shield plates that are formed of lead or the like and shield the radiation R are disposed on respective sides of a quadrangle, and a quadrangular opening through which the radiation R is transmitted is formed in a center portion. The irradiation field limiter 50 changes the irradiation field of the radiation R by changing the position of each shield plate to change the size of the opening.

The tube voltage generator 18 and the irradiation switch 19 are connected to the radiation source control device 17. The radiation source control device 17 controls the operation of the radiation source 16 in response to instruction signals from the irradiation switch 19. The irradiation switch 19 is operated in a case where the operator instructs the radiation source 16 to start the irradiation with the radiation R.

For example, the irradiation switch 19 is a two-stage motion switch. In a case where the operator pushes the irradiation switch 19 to the first stage, the anode starts to rotate and is in a preparation state. Moreover, in a case where the operator pushes the irradiation switch 19 to the second stage, the tube voltage is applied between the anode and the cathode from the tube voltage generator 18, and thereby the radiation R is generated.

The imaging conditions are set in the radiation source control device 17. The imaging condition is a condition defined by the tube voltage, the tube current, and the tube current time product (product of the tube current and the irradiation time) applied to the radiation tube 49. In a case where an instruction to start the irradiation with the radiation R is given by the operation of the irradiation switch 19, the radiation source control device 17 operates the tube voltage generator 18 on the basis of the set imaging conditions to emit the radiation R from the radiation tube 49. The tube voltage generator 18 generates the tube voltage by boosting an input voltage with a transformer. The tube voltage generated by the tube voltage generator 18 is supplied to the radiation tube 49.

The distance measurement camera 20 has a light transmission unit and a light receiving unit (not illustrated), and is configured to measure a distance from the distance measurement camera 20 to a surface of the holder 37 and a surface of the subject H by measuring a time after measurement light B is emitted from the light transmission unit toward the subject H until the light receiving unit receives the measurement light B reflected on a surface of the subject H. For example, the measurement light B is infrared laser light. In addition, the measurement light B may be pulse light, or may be intensity-modulated continuous light. In a case where continuous light is used as the measurement light B, a phase difference between the measurement light B emitted from the light transmission unit and the measurement light B received by the light receiving unit is obtained to measure the time. For example, the distance measurement camera 20 according to the present embodiment measures a distance to one of measurement objects. The measurement value obtained by the distance measurement camera 20 is output to the console 14. Note that the distance measurement camera 20 may be built in the irradiation field limiter 50.

Figure 2:
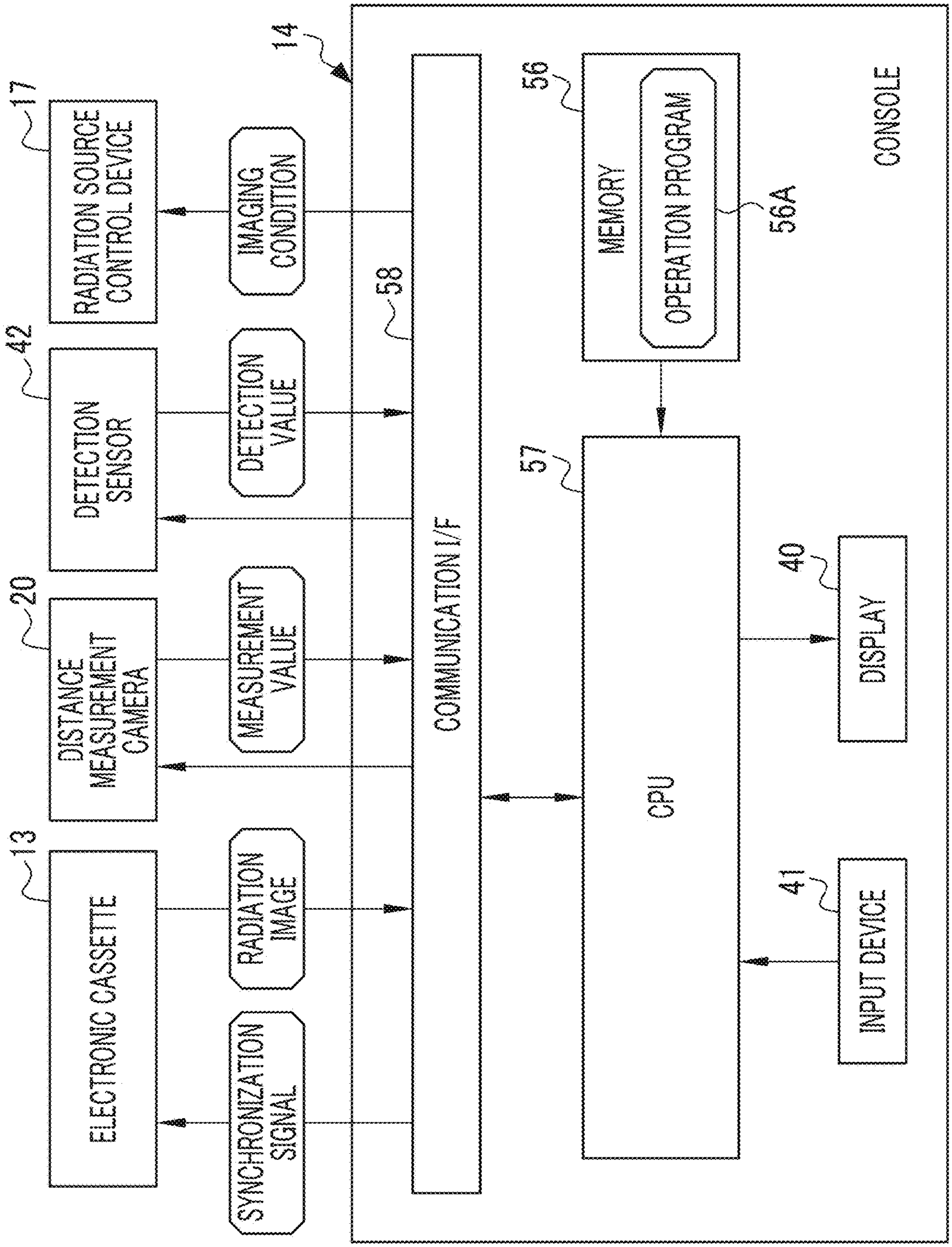
FIG. 2 is a block diagram illustrating a configuration example of a console.

FIG. 2 illustrates a configuration example of the console 14. The console 14 includes a memory 56, a central processing unit (CPU) 57, and a communication interface (I/F) 58 in addition to the display 40 and the input device 41 described above. The display 40, the input device 41, the memory 56, the CPU 57, and the communication I/F 58 are connected to each other.

The memory 56 is a storage device such as a flash memory that is built in or connected to the CPU 57. The memory 56 stores an operation program 56A, various kinds of data, and the like. The CPU 57 executes processing on the basis of the operation program 56A stored in the memory 56. Accordingly, the CPU 57 integrally controls each unit of the computer. The CPU 57 is an example of a "processor" according to the technology of the present disclosure. The communication I/F 58 controls transmission of various kinds of information with an external device such as the electronic cassette 13.

The CPU 57 displays a plurality of kinds of imaging menus on the display 40 in a selectable form. The imaging menu defines an imaging technique in which an imaging part of the subject H, an imaging posture of the subject H, and an imaging direction of the subject H are set as one set, such as "chest, upright, front". The operator operates the input device 41 to register one imaging menu among the plurality of kinds of imaging menus. In the present embodiment, a case where the upright posture is selected as the imaging posture will be described.

The CPU 57 acquires the measurement value output from the distance measurement camera 20 and the detection value output from the detection sensor 42 via the communication I/F 58 before starting the radiography, and calculates a body thickness TB of the subject H on the basis of information including the acquired measurement value and detection value. In addition, the CPU 57 determines the imaging condition on the basis of the imaging menu and the calculated body thickness TB, and transmits the determined imaging condition to the radiation source control device 17 via the communication I/F 58.

In a case where an instruction to start the irradiation with the radiation R is given to the radiation source control device 17 via the irradiation switch 19, the CPU 57 receives an irradiation start signal indicating that the irradiation with the radiation R is started, from the radiation source control device 17. In a case where the irradiation start signal is received, the CPU 57 transmits a synchronization signal indicating that the irradiation with the radiation R is started, to the electronic cassette 13. Furthermore, the CPU 57 receives an irradiation end signal indicating that the irradiation with the radiation R is ended, from the radiation source control device 17. In a case where the irradiation end signal is received, the CPU 57 transmits a synchronization signal indicating that the irradiation with the radiation R is ended, to the electronic cassette 13.

In a case where the synchronization signal indicating that the irradiation with the radiation R is started is received from the console 14, the electronic cassette 13 causes the detection panel to start an accumulation operation. In addition, in a case where the synchronization signal indicating that the irradiation with the radiation R is ended is received from the console 14, the electronic cassette 13 causes the detection panel to start a readout operation.

The CPU 57 receives the radiation image from the electronic cassette 13 via the communication I/F 58. The CPU 57 performs various kinds of image processing on the radiation image, and then displays the radiation image on the display 40 to provide the radiation image for the operator to browse.

Figure 3:
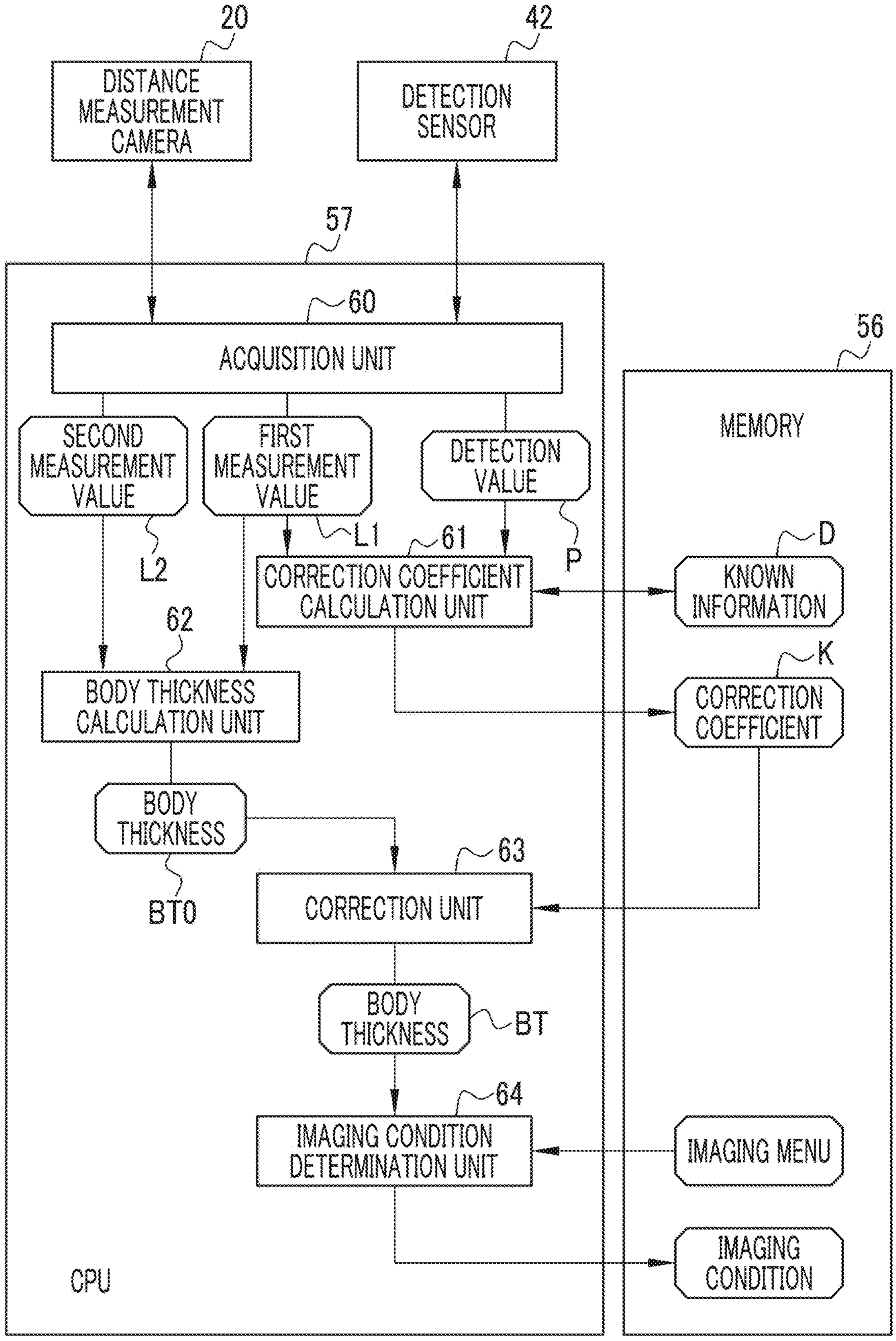
FIG. 3 is a block diagram illustrating an example of a function related to determination of an imaging condition.

FIG. 3 illustrates an example of a function related to determination of an imaging condition configured in the CPU 57. The CPU 57 executes processing on the basis of the operation program 56A to function as an acquisition unit 60, a correction coefficient calculation unit 61, a body thickness calculation unit 62, a correction unit 63, and an imaging condition determination unit 64. In the present embodiment, the CPU 57, the memory 56, the distance measurement camera 20, and the detection sensor 42 constitute a "distance measurement device" according to the technology of the present disclosure.

The acquisition unit 60 acquires a detection value P output from the detection sensor 42 by controlling the detection sensor 42. The detection value P is a value corresponding to the SID (refer to FIG. 4). The relationship between the detection value P and the SID may be stored in the memory 56 in advance.

In addition, the acquisition unit 60 acquires a first measurement value L1 and a second measurement value L2 output from the distance measurement camera 20 by controlling the distance measurement camera 20. The first measurement value L1 is a measurement value in a state where the subject H is not disposed, and represents a distance from the distance measurement camera 20 to the surface of the holder 37 (refer to FIG. 4). The second measurement value L2 is a measurement value in a state where the subject H is disposed, and represents a distance from the distance measurement camera 20 to the surface of the subject H (refer to FIG. 4).

The correction coefficient calculation unit 61 calculates a correction coefficient K using the SID corresponding to the detection value P, the first measurement value L1, and known information D stored in the memory 56. Specifically, the correction coefficient calculation unit 61 calculates the correction coefficient K on the basis of Expressions (1A) and (1B). The correction coefficient calculation unit 61 stores the calculated correction coefficient K in the memory 56.

$$K = LP/L1 \tag{1A}$$

$$LP = SID - \Delta 1 - \Delta 2 \tag{1B}$$

Figure 4:
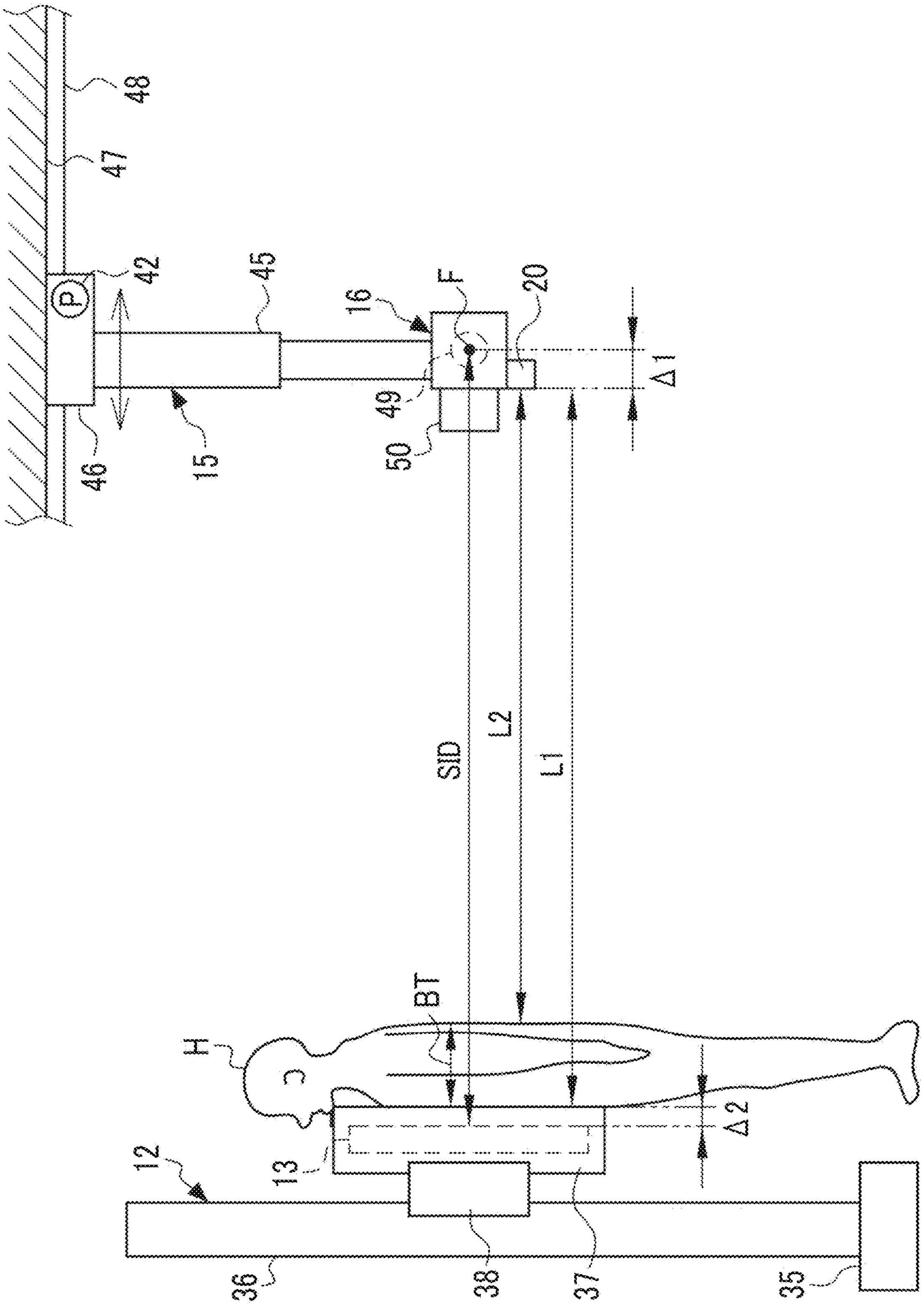
FIG. 4 is a diagram illustrating a positional relationship between a radiation source, a distance measurement camera, and an upright imaging stand.

Here, Δ1 is a distance between the distance measurement camera 20 and the focal point F of the radiation R (refer to FIG. 4). 42 is a distance from the surface of the holder 37 to the detection surface of the electronic cassette 13 (refer to FIG. 4). The distances Δ1 and Δ2 are known, and are included in the known information D. That is, LP is a known distance obtained from the device information, and represents a distance from the distance measurement camera 20 to the surface of the holder 37. Note that the holder 37 is an example of a "reference object of which a distance is known" according to the technology of the present disclosure.

In a case where the measurement accuracy of the distance measurement camera 20 is high, K=1 should be satisfied. However, since the measurement value obtained by the distance measurement camera 20 is changed with time due to the temperature drift, K=1 is not obtained particularly in a case where the elapsed time from the time of power supply turn-on of the distance measurement camera 20 is short. The correction coefficient K is a correction coefficient for correcting the temperature drift of the measurement value obtained by the distance measurement camera 20.

The body thickness calculation unit 62 calculates a body thickness BT0 of the subject H by using the first measurement value L1 and the second measurement value L2. Specifically, the body thickness calculation unit 62 calculates the body thickness BT0 by subtracting the second measurement value L2 from the first measurement value L1 on the basis of Expression (2).

$$BT0 = L1 - L2 \tag{2}$$

Since the body thickness BT0 is a value before correction including an influence of the temperature drift, the body thickness BT0 is hereinafter referred to as a primary body thickness BT0. The primary body thickness BT0, which is a difference value between the first measurement value L1 and the second measurement value L2, is an example of a "calculation value calculated by using the second measurement value" according to the present embodiment.

The correction unit 63 calculates a body thickness BT of the subject H by using the primary body thickness BT0 and the correction coefficient K read out from the memory 56. Specifically, the correction unit 63 calculates the body thickness BT in which the temperature drift is corrected, by multiplying the primary body thickness BT0 by the correction coefficient K on the basis of Expression (3).

$$BT = BT0 \times K \quad (3)$$

The imaging condition determination unit 64 determines the imaging condition on the basis of the imaging menu registered by the operator operating the input device 41 and the body thickness TB corrected by the correction unit 63. Specifically, as the body thickness TB is larger, the tube current and the tube current time product are larger. The imaging condition determination unit 64 stores the determined imaging condition in the memory 56.

Figure 5:
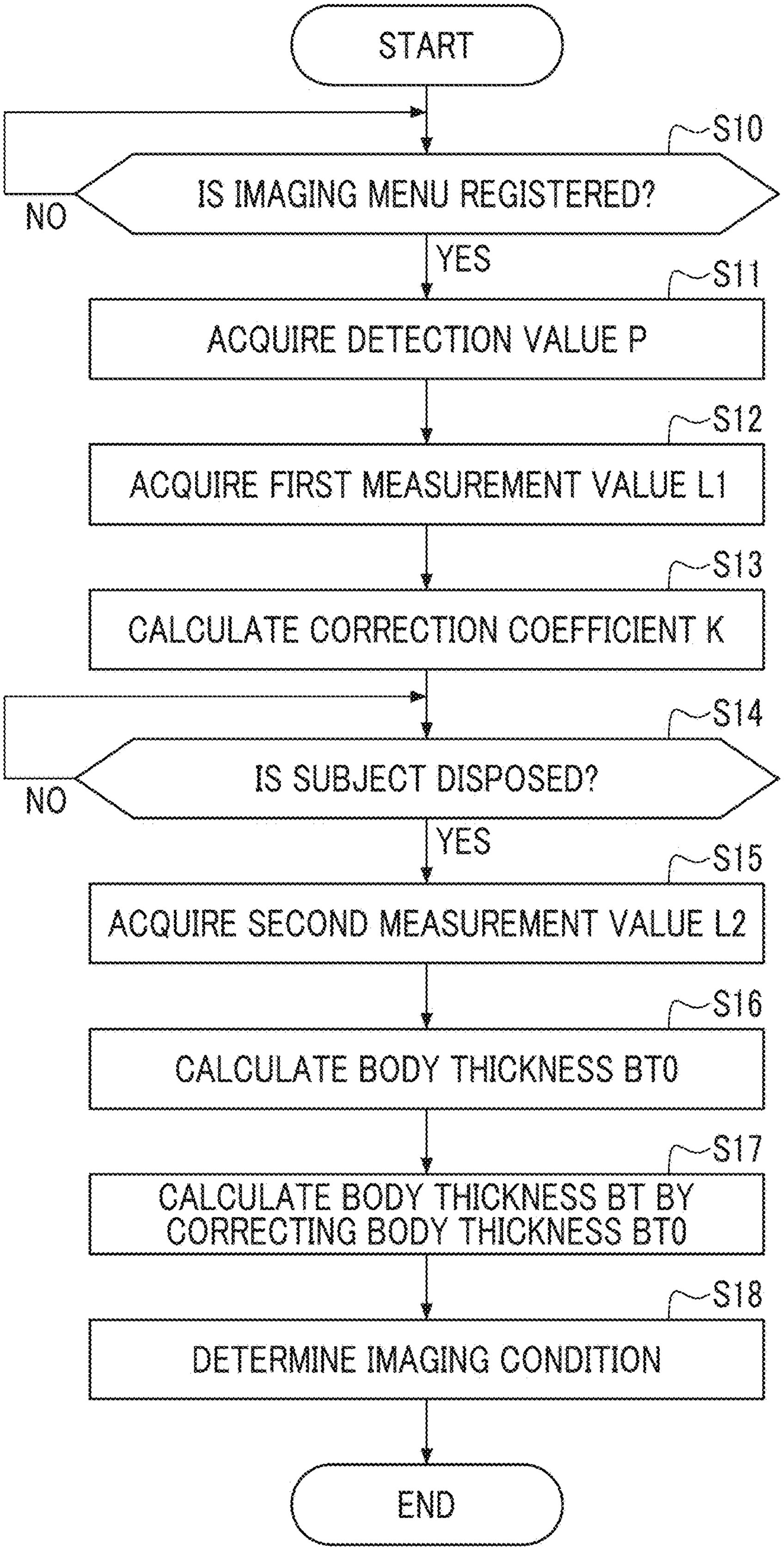
FIG. 5 is a flowchart illustrating an example of a flow of imaging condition determination processing.

FIG. 5 illustrates an example of a flow of imaging condition determination processing by the CPU 57. First, the CPU 57 determines whether or not the imaging menu is registered by the operator operating the input device 41 (step S10). In a case where the imaging menu is not registered (step S10: NO), the CPU 57 repeats step S10.

In a case where the imaging menu is registered (step S10: YES), the CPU 57 acquires the detection value P from the detection sensor 42 by the acquisition unit 60 (step S11). Next, the CPU 57 acquires the first measurement value L1 from the distance measurement camera 20 by the acquisition unit 60 (step S12). Note that, in this case, the subject H is not disposed on the upright imaging stand 12. In addition, the detection value P may be acquired in advance before the imaging menu is registered.

Next, the CPU 57 calculates the correction coefficient K as described above by using the detection value P, the first measurement value L1, and the known information D, by the correction coefficient calculation unit 61 (step S13).

Next, the CPU 57 determines whether or not the subject H is disposed on the upright imaging stand 12 (step S14). For example, the CPU 57 determines whether or not the subject H is disposed on the basis of whether or not the operator inputs that the subject H is disposed, by operating the input device 41. In a case where the subject H is not disposed (step S14: NO), the CPU 57 repeats step S14. In a case where the subject His disposed (step S14: YES), the CPU 57 acquires the second measurement value L2 from the distance measurement camera 20 by the acquisition unit 60 (step S15).

Next, the CPU 57 calculates the primary body thickness BT0 as described above by using the first measurement value L1 and the second measurement value L2, by the body thickness calculation unit 62 (step S16). Next, the CPU 57 calculates the body thickness BT in which the temperature drift is corrected as described above by correcting the primary body thickness BT0 using the correction coefficient K by the correction unit 63 (step S17).

Then, the CPU 57 determines the imaging conditions as described above by using the imaging menu and the body thickness BT by the imaging condition determination unit 64 (step S18). Thereby, the imaging condition determination processing is ended.

The imaging condition determined by the imaging condition determination processing is transmitted to the radiation source control device 17. Thereafter, in a case where the irradiation switch 19 is operated, radiography is performed on the basis of the imaging condition transmitted to the radiation source control device 17.

For example, in a case of SID=1200 mm, Δ1=100 mm, and Δ2=20 mm, LP=1080 mm is obtained. In addition, in a case of L1=1050 mm, K=1.029 is obtained. In a case of L2=850 mm, BT0=200 mm is obtained, but by the correction using the correction coefficient K, BT=205.7 mm is obtained.

As described above, in the present embodiment, the correction coefficient K is calculated by dividing the known distance by the measurement value measured by the distance measurement camera 20, and the measurement value obtained by the distance measurement camera 20 is corrected using the correction coefficient K. Therefore, the measurement can be performed before the temperature drift is stabilized. That is, according to the technology of the present disclosure, it is possible to perform measurement quickly with high accuracy.

Note that, in the above-described embodiment, the body thickness BT of the subject H disposed in the upright state with respect to the upright imaging stand 12 is measured, but the body thickness BT of the subject H disposed in a decubitus state with respect to a decubitus imaging table (not illustrated) can also be measured. In this case, the value of the SID need only be obtained on the basis of the detection value of the position in the vertical direction by the detection sensor such as a potentiometer or a linear encoder built in the radiation source suspension device 15.

Figure 6:
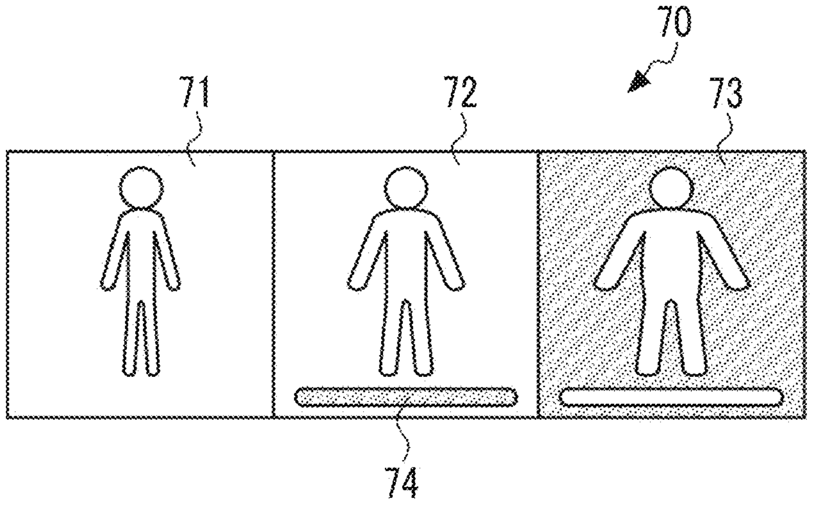
FIG. 6 is a diagram illustrating an example of an icon representing a plurality of imaging conditions.

In addition, in the above-described embodiment, the CPU 57 determines the imaging condition corresponding to the body thickness BT obtained by the measurement with the distance measurement camera 20, but may be configured to propose the imaging condition corresponding to the obtained body thickness BT to the operator to enable the operator to finally determine the imaging condition to be used in the radiography. For example, as illustrated in FIG. 6, the CPU 57 displays an icon 70 representing a plurality of imaging conditions 71 to 73 including imaging condition corresponding to the obtained body thickness BT on the display 40, and causes the operator to select any of the imaging conditions 71 to 73 included in the displayed icon 70 by using the input device 41. The imaging condition 71 is an imaging condition corresponding to a thin person. The imaging condition 72 is an imaging condition corresponding to a person with a normal physique. The imaging condition 73 is an imaging condition corresponding to a fat person.

In the example illustrated in FIG. 6, the CPU 57 displays a bar 74 on the imaging condition 72 corresponding to the body thickness BT obtained by the measurement by the distance measurement camera 20 to indicate that the imaging condition is the optimum imaging condition to be proposed to the operator. The operator can also select the imaging condition other than the proposed imaging condition 72 by using the input device 41. In the example illustrated in FIG. 6, the operator selects the imaging condition 73. The CPU 57 transmits the selected imaging condition to the radiation source control device 17.

Figure 7:
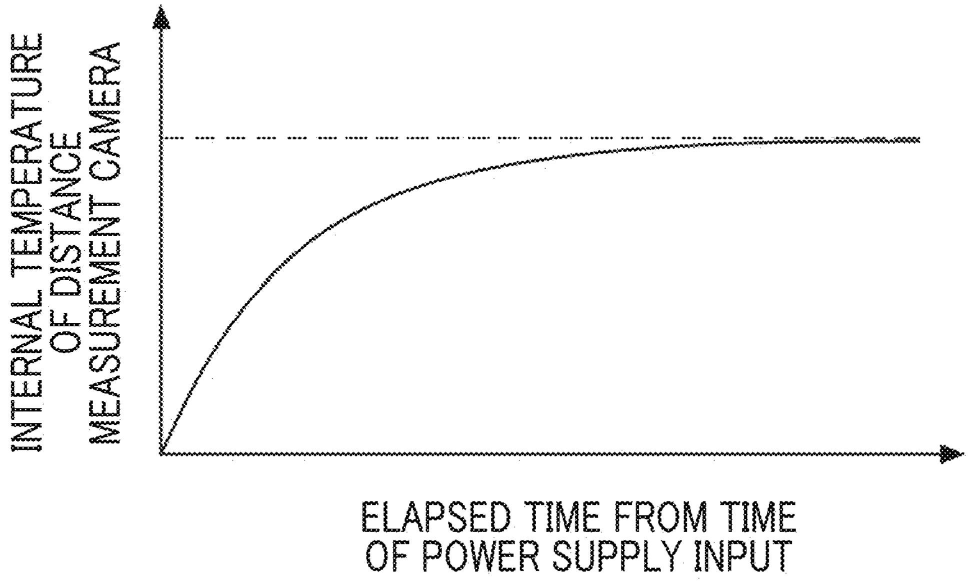
FIG. 7 is a diagram illustrating an example of a relationship between an internal temperature of the distance measurement camera and an elapsed time from a time of power supply turn-on, FIG. 8 is a diagram illustrating an example of an update timing of correction coefficients.
Figure 8:
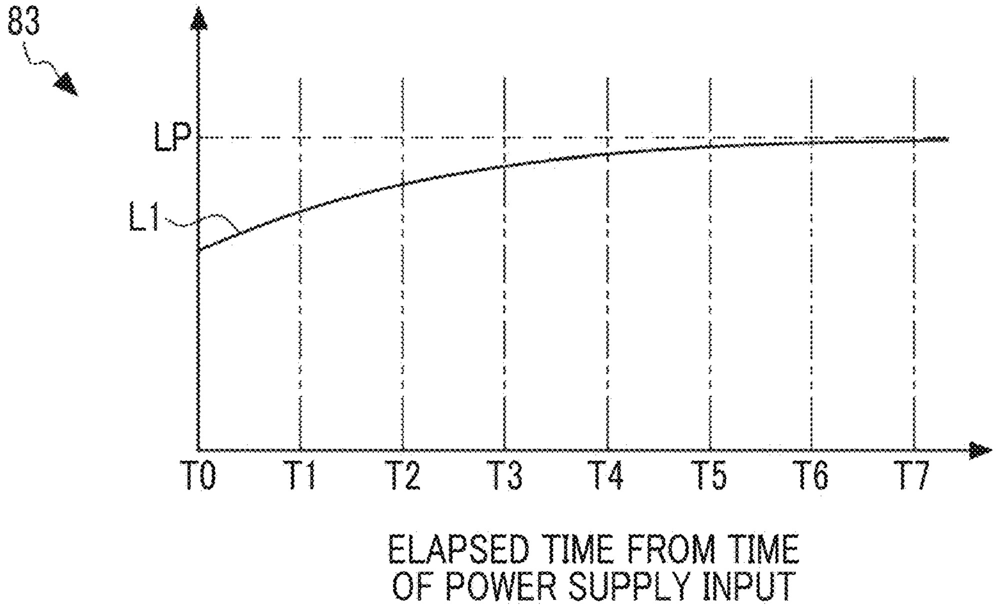

In addition, in the above-described embodiment, the CPU 57 acquires the first measurement value L1 and calculates the correction coefficient K in a case where the imaging menu is registered, but after the power supply of the distance measurement camera 20 is turned on, the CPU 57 may execute the acquisition of the first measurement value L1 and the calculation of the correction coefficient K periodically. This is because, as illustrated in FIG. 7, the internal temperature of the distance measurement camera 20 is changed in accordance with the elapsed time from the time of power supply turn-on. In this way, the internal temperature is changed, so that a temperature drift as illustrated in FIG. 8 occurs in the first measurement value L1, and the correction coefficient K is changed. T0 to T7 illustrated in FIG. 8 represent update timings at which the first measurement value L1 is acquired and the correction coefficient K is calculated. An interval of the update timing is, for example, 30 minutes. The correction coefficient K calculated at each update timing is overwritten in the memory 56. That is, the correction coefficient K is updated for each constant time. In this case, the CPU 57 calculates the body thickness BT by acquiring the second measurement value L2 and calculating the primary body thickness BT0, and then correcting the primary body thickness BT0 using the correction coefficient K updated at the immediately preceding update timing.

Figure 9:
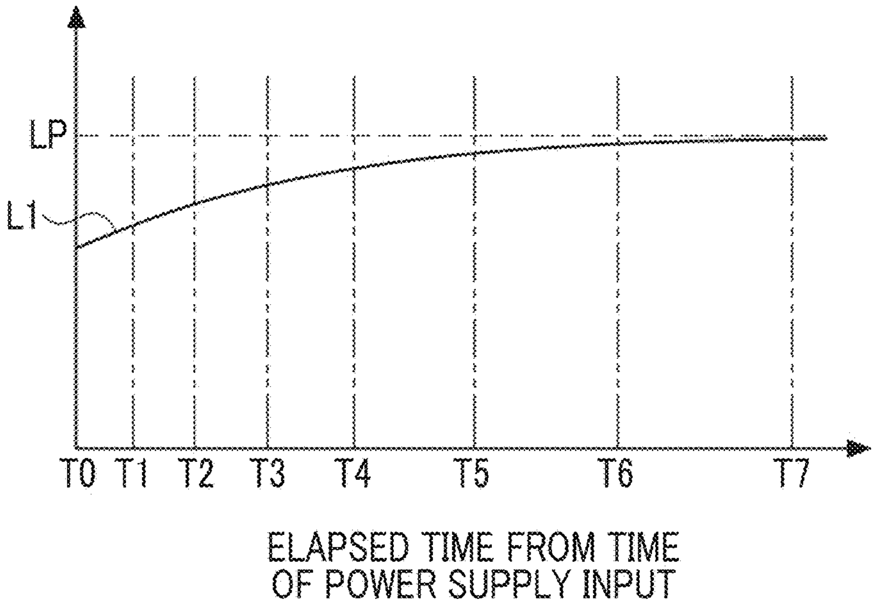
FIG. 9 is a diagram illustrating another example of update timing of correction coefficients.

In addition, the interval of the update timing may not be fixed. Since the temperature change is larger as the elapsed time from the time of power supply turn-on is shorter, as illustrated in FIG. 9, the interval of the update timing may be shortened as the elapsed time from the time of power supply turn-on is shorter. That is, the update frequency may be decreased as the number of times of updating the correction coefficient K is increased. In addition, the correction coefficient K may not be updated after the rate of change in the temperature change (that is, the temperature gradient) is equal to or less than a certain value.

In addition, in the above-described embodiment, the CPU 57 acquires the second measurement value L2 from the distance measurement camera 20 in a case where the subject H is disposed. However, the CPU 57 may acquire the second measurement value L2 from the distance measurement camera 20 in a case where it is detected that the operator has pushed the irradiation switch 19 to the first stage.

In addition, in the above-described embodiment, the CPU 57 calculates the body thickness BT by calculating the primary body thickness BT0 and then correcting the primary body thickness BT0 using the correction coefficient K. Instead of this, the CPU 57 may calculate the body thickness BT by correcting each of the first measurement value L1 and the second measurement value L2 using the correction coefficient K, and then subtracting the corrected second measurement value L2 from the corrected first measurement value L1.

In addition, in the above-described embodiment, the measurement value obtained by measuring the distance from the distance measurement camera 20 to the reference object (the holder 37 in the above-described embodiment) once by using the distance measurement camera 20 is set as the first measurement value L1. Instead of this, an average value of the plurality of measurement values obtained by measuring the distance from the distance measurement camera 20 to the reference object a plurality of times by using the distance measurement camera 20 may be set as the first measurement value L1. Accordingly, since the accuracy of the first measurement value L1 is improved, the accuracy of the correction coefficient K is improved.

The above-described embodiment is an example in which the distance measurement device is applied to the radiography system, but the distance measurement device according to the technology of the present disclosure is not limited to the medical field such as the radiography, and can be applied to other fields.

Second Embodiment

Figure 10:
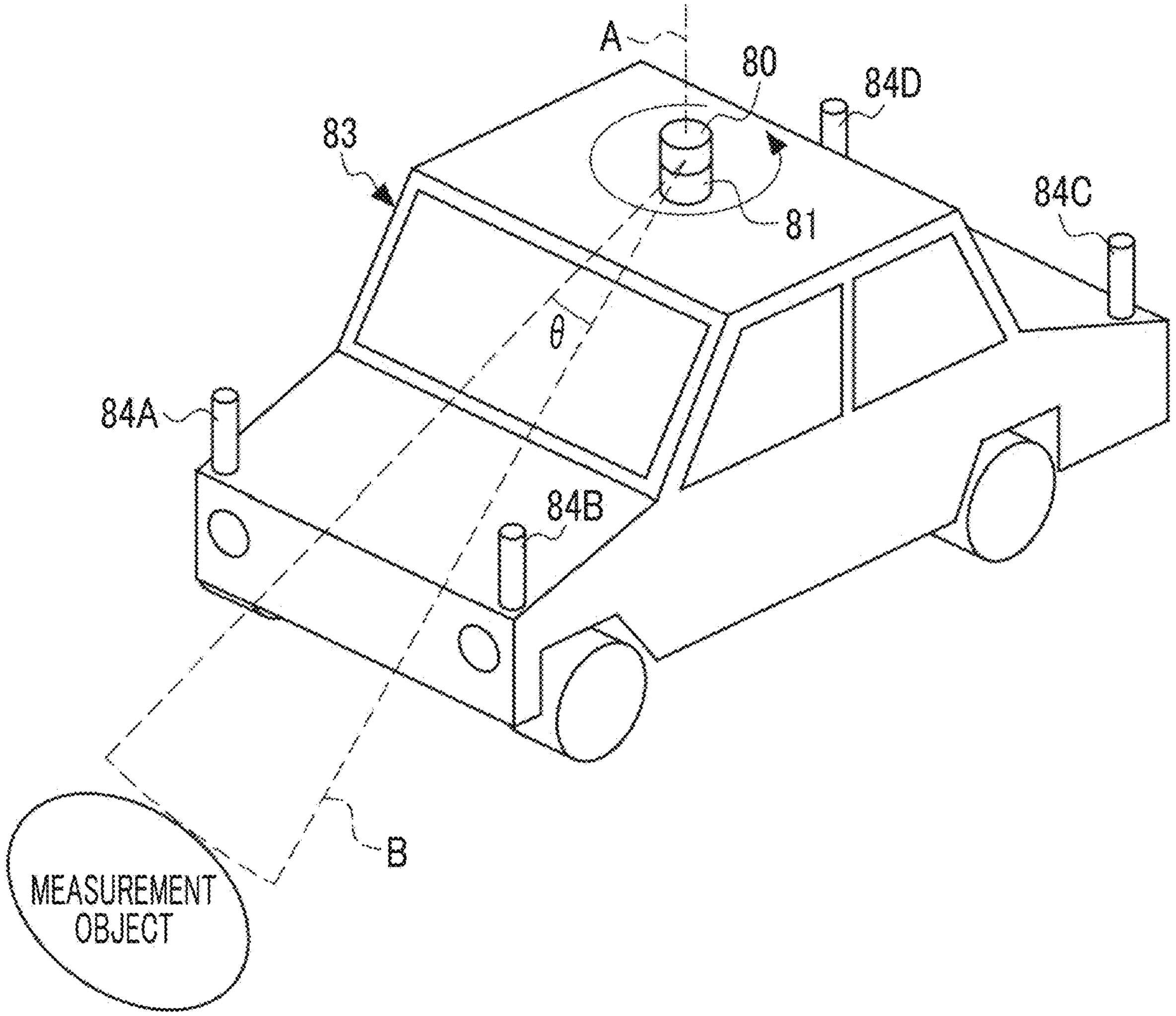
FIG. 10 is a perspective view illustrating a vehicle on which a distance measurement device according to a second embodiment is mounted.

FIG. 10 illustrates a vehicle on which a distance measurement device according to a second embodiment is mounted. As illustrated in FIG. 10, the distance measurement device according to the present embodiment includes a ToF type distance measurement camera 80 and a rotation device 81. The rotation device 81 is attached to an upper portion of a vehicle body 83, and rotates the distance measurement camera 80 by 360° about a rotation axis A. The distance measurement camera 80 and the rotation device 81 constitute a so-called light detection and ranging (LiDAR) device, and measure a distance to a measurement object present around the vehicle body 83.

The distance measurement camera 80 has the same configuration as the distance measurement camera 20 according to the first embodiment, and measures the distance to the measurement object by measuring a time from after measurement light B is emitted from the light transmission unit until the light receiving unit receives the measurement light B reflected on the surface of the subject H. The distance measurement camera 80 may have a two-dimensional sensor, and may acquire distance information in an angle of view θ for each pixel for each time of distance measurement.

A plurality of reference objects 84A to 84D are provided in the vehicle body 83. The reference objects 84A to 84D are, for example, poles fixed to corner portions of the vehicle body 83.

Figure 11:
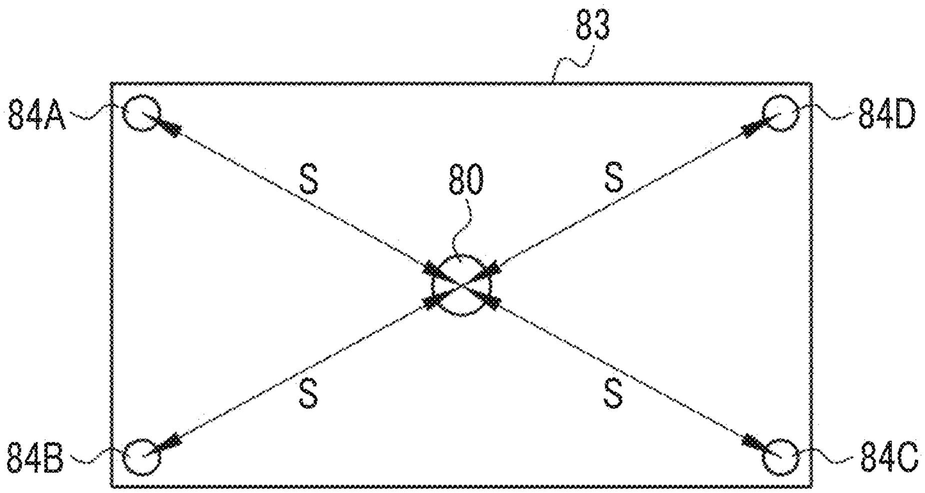
FIG. 11 is a diagram illustrating an example of a positional relationship between the distance measurement camera and a plurality of reference objects.

FIG. 11 illustrates an example of a positional relationship between the distance measurement camera 80 and the reference objects 84A to 84D. FIG. 11 schematically illustrates a view of the vehicle body 83 as viewed from above. A distance S between the distance measurement camera 80 and each of the reference objects 84A to 84D is equal and known. For example, the distance S is 1000 mm.

Figure 12:
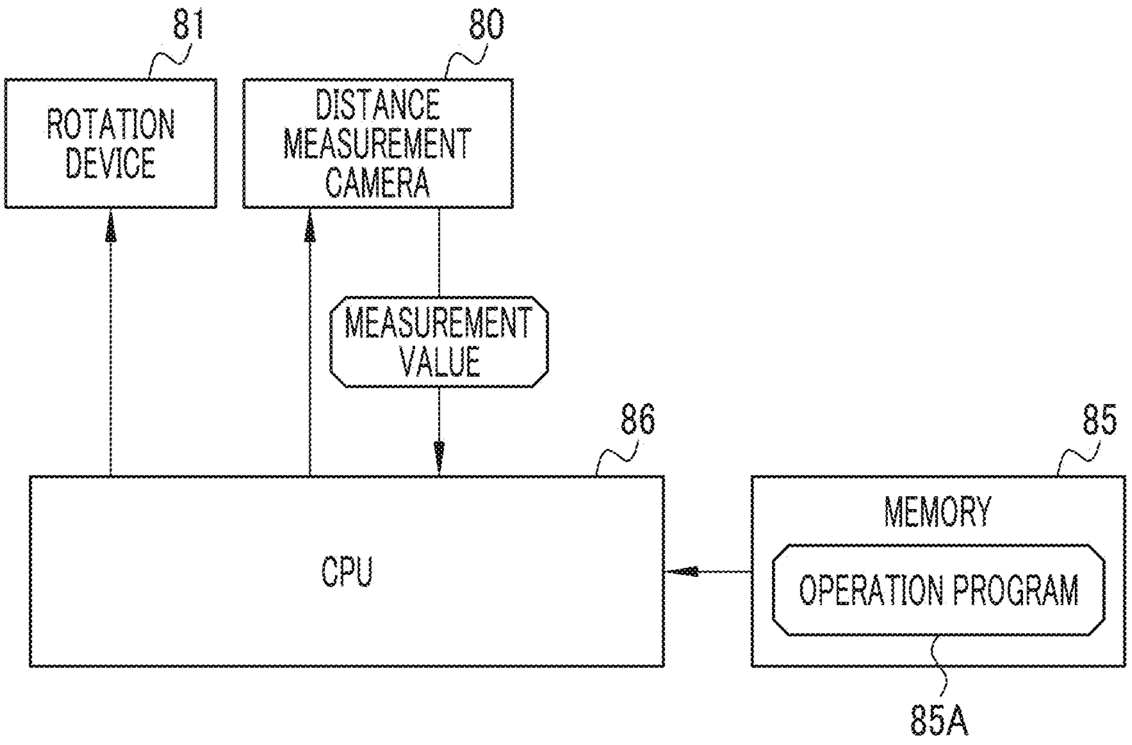
FIG. 12 is a block diagram illustrating a configuration example of the distance measurement device according to the second embodiment.

FIG. 12 illustrates a configuration example of the distance measurement device according to the second embodiment. The distance measurement device according to the present embodiment includes the distance measurement camera 80, the rotation device 81, a memory 85, and a CPU 86. The memory 85 and the CPU 86 have the same configuration as the memory 56 and the CPU 57 according to the first embodiment. The memory 85 stores an operation program 85A, various kinds of data, and the like. The CPU 86 is an example of a "processor" according to the technology of the present disclosure.

Figure 13:
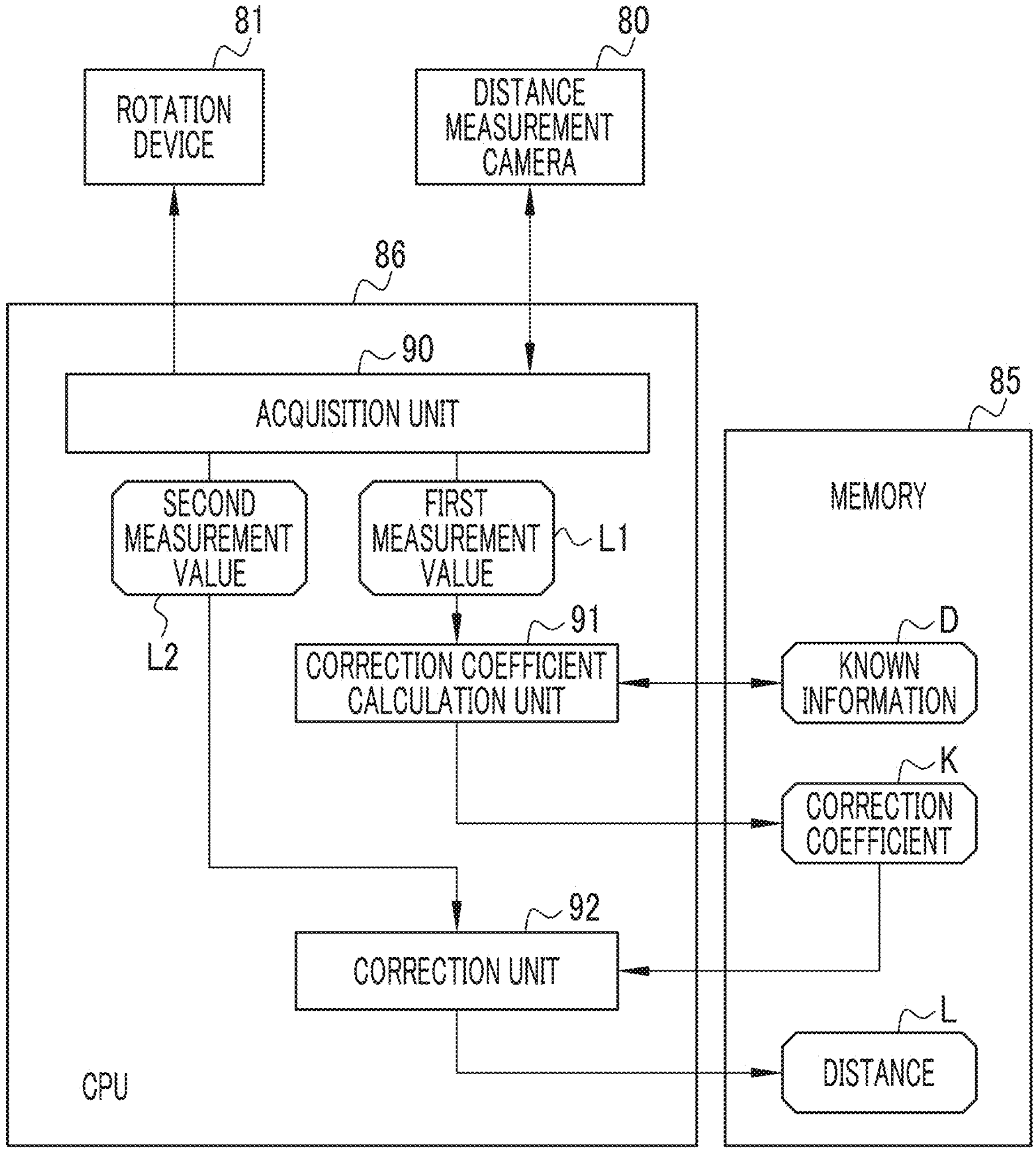
FIG. 13 is a block diagram illustrating an example of a function related to distance measurement.

FIG. 13 illustrates an example of a function related to distance measurement configured in the CPU 86. The CPU 86 executes processing on the basis of the operation program 85A to function as an acquisition unit 90, a correction coefficient calculation unit 91, and a correction unit 92.

The acquisition unit 90 controls the distance measurement camera 80 to acquire the first measurement value L1 and the second measurement value L2 output from the distance measurement camera 80 in a state where the rotation device 81 is controlled to rotate the distance measurement camera 80. In the present embodiment, the first measurement value L1 is a measurement value of the distance from the distance measurement camera 80 to each of the reference objects 84A to 84D. The second measurement value L2 is a measurement value of the distance from the distance measurement camera 80 to the measurement object.

Figure 14:
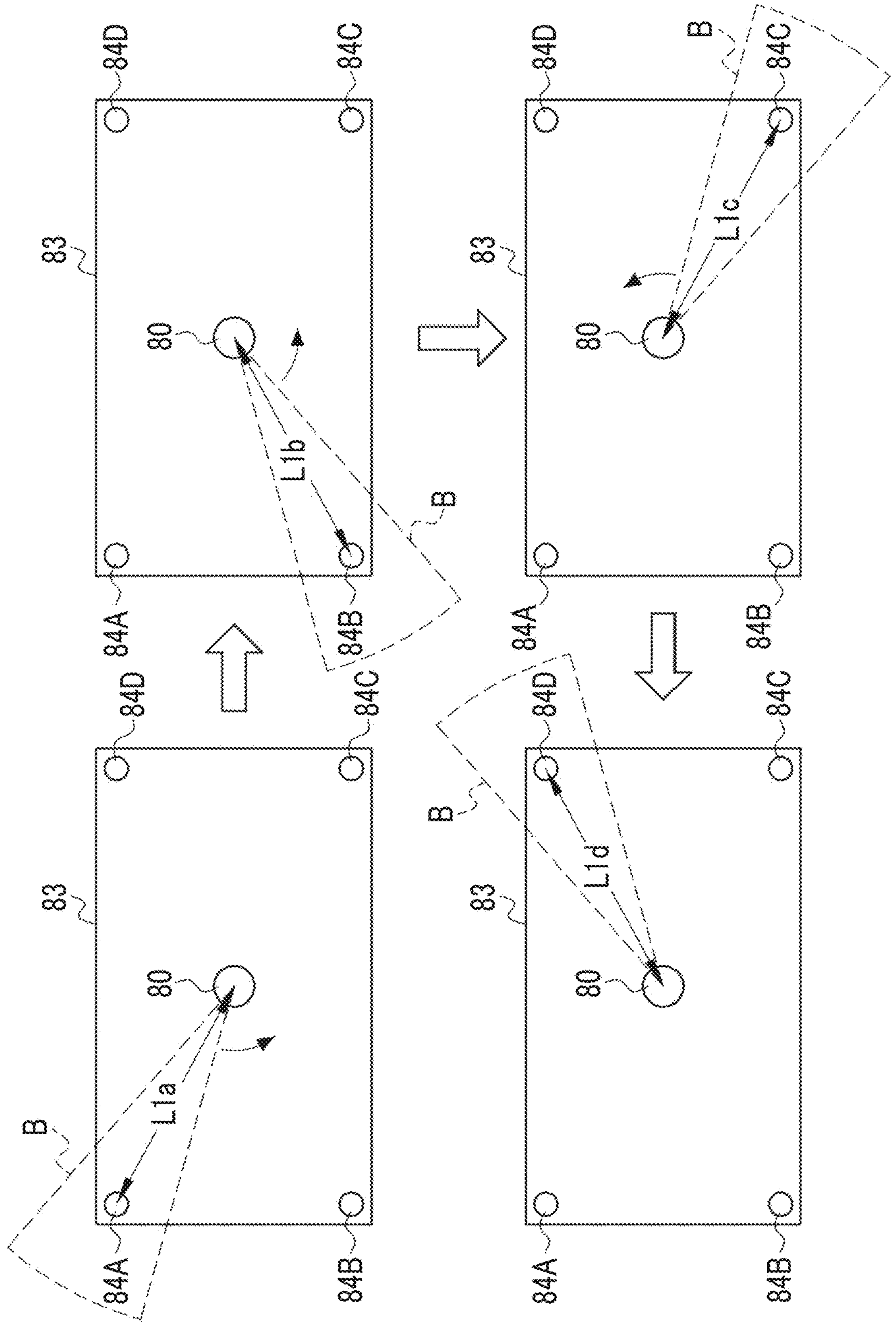
FIG. 14 is a diagram illustrating a method of acquiring a first measurement value.

Specifically, as illustrated in FIG. 14, the acquisition unit 90 acquires a first measurement value L1a of the distance from the distance measurement camera 80 to the reference object 84A, a first measurement value L1b of the distance from the distance measurement camera 80 to the reference object 84B, a first measurement value L1c of the distance from the distance measurement camera 80 to the reference object 84C, and a first measurement value L1d of the distance from the distance measurement camera 80 to the reference object 84D.

The correction coefficient calculation unit 91 calculates the correction coefficient K using the first measurement values L1a to L1d and the known information D stored in the memory 85. In the present embodiment, the known information D is the distance S described above. Specifically, the correction coefficient calculation unit 91 calculates the correction coefficient K on the basis of Expressions (4A) and (4B). The correction coefficient calculation unit 91 stores the calculated correction coefficient K in the memory 85.

$$K = S/L1av \quad (4A)$$

$$L1av = (L1a + L1b + L1c + L1d)/4 \quad (4B)$$

Here, L1av is an average value of the first measurement values L1a to L1d. In a case where the measurement accuracy of the distance measurement camera 80 is high, K=1 should be satisfied. However, since the measurement value obtained by the distance measurement camera 80 is changed with time due to the temperature drift, K=1 is not obtained particularly in a case where the elapsed time from the time of power supply turn-on of the distance measurement camera 80 is short.

The correction unit 92 calculates a distance L to the measurement object by using the second measurement value L2 and the correction coefficient K read out from the memory 85. Specifically, the correction unit 92 calculates the distance L to the measurement object by multiplying the second measurement value L2 by the correction coefficient K on the basis of Expression (5).

$$L = L2 \times K \quad (5)$$

As described above, in the present embodiment, since the correction coefficient K is calculated using the average value of the measurement values of the distances to the plurality of reference objects 84A to 84D, the correction accuracy is improved, and the measurement can be performed with high accuracy. Note that the number of reference objects is not limited to four, and can be appropriately changed. In addition, the kind, arrangement, and the like of the reference object can be appropriately changed.

In addition, in the present embodiment, since the distance measurement camera 80 is rotated by the rotation device 81, it is possible to prevent the reference object that is not originally desired to be imaged from being imaged.

It is assumed that a range of a measurement distance by the distance measurement device according to the present embodiment is about 0.5 m to 2 m, and the required measurement accuracy is about +30 mm. In this case, the distance measurement device according to the present embodiment can be used in a case of measuring a distance to an obstacle present within 2 m from the vehicle body in a case of parking the vehicle. For example, in a case where an error of a measurement value of the distance to the obstacle exceeds ±30 mm, there is a high risk that the vehicle body comes into contact with the obstacle. With the distance measurement device according to the present embodiment, it is possible to reduce a contact risk with the obstacle during parking.

Note that the distance measurement device according to the present embodiment can be mounted on another moving object without being limited to the vehicle.

Third Embodiment

Figure 15:
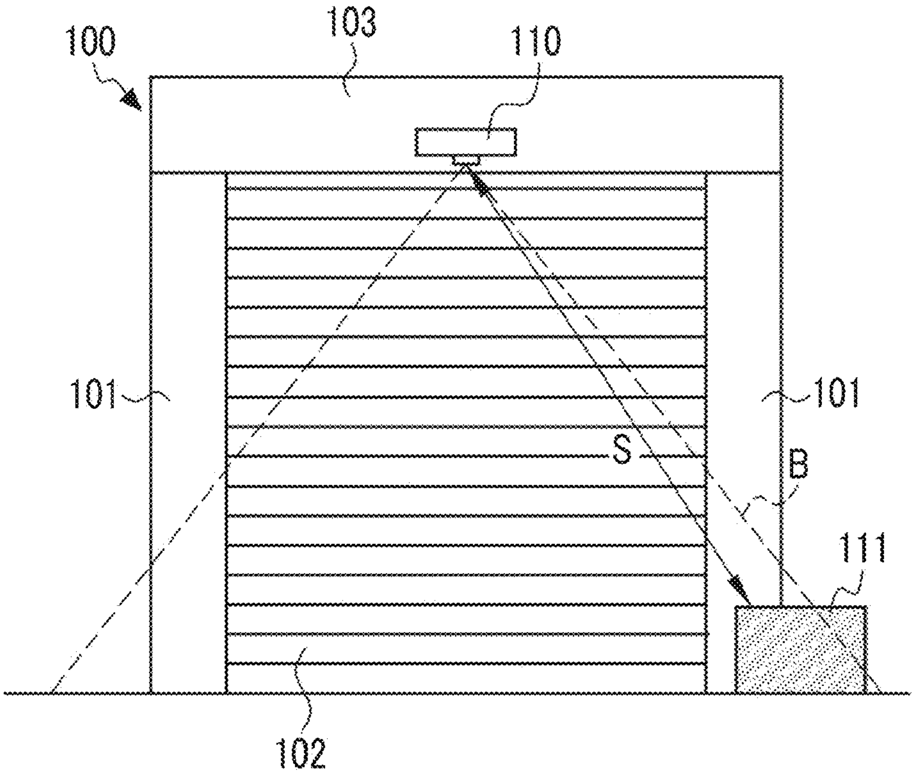
FIG. 15 is a front view of a shutter device.
Figure 16:
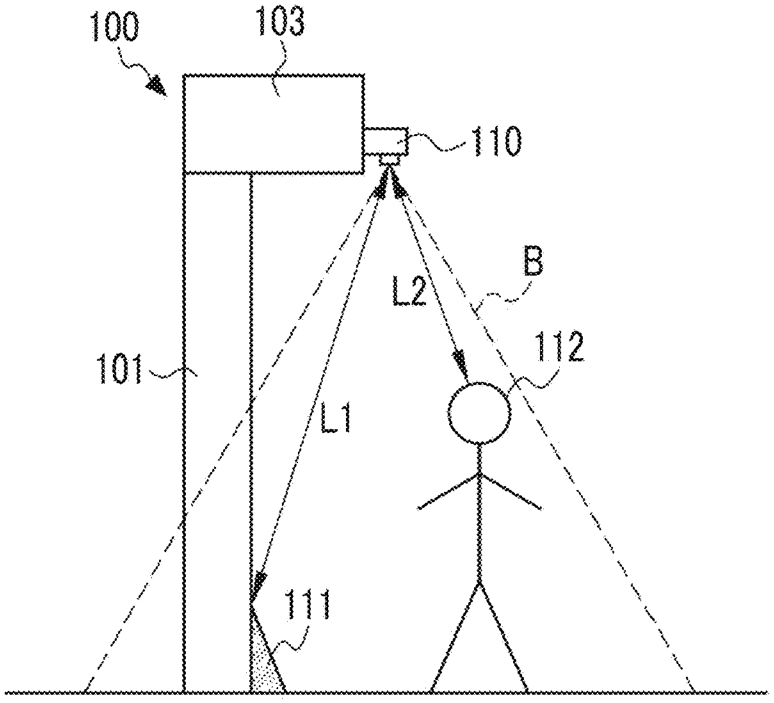
FIG. 16 is a side view of the shutter device.

FIGS. 15 and 16 illustrate a shutter device 100 to which a distance measurement device according to a third embodiment is attached. FIG. 15 is a front view of the shutter device 100. FIG. 16 is a side view of the shutter device 100.

The shutter device 100 is provided in an opening portion that is an entrance and an exit of a structure such as a building, and opens and closes a shutter curtain 102 that is an opening and closing body, for example, along a pair of guide rails 101. A shutter case 103 in which a winding shaft that winds the shutter curtain 102, a motor that rotationally drives the winding shaft, a control device that controls the motor, and the like are built is provided on an upper portion of the guide rail 101.

A ToF type distance measurement camera 110 that can measure a distance to an obstacle present in a downward direction is attached to a front surface of the shutter case 103. The distance measurement device according to the present embodiment includes the distance measurement camera 110, a memory (not illustrated), and a CPU (not illustrated). The distance measurement device according to the present embodiment has the same configuration as the distance measurement device according to the second embodiment, except that the distance measurement camera 110 is not configured to be rotatable.

A reference object 111 is provided near the ground on one of the pair of guide rails 101. It is preferable that the reference object 111 is provided at a position that does not inhibit the opening and closing of the shutter curtains 102 and does not inhibit the opening portion in a state where the shutter curtain 102 is opened. Note that the reference object 111 may be integrally formed with the guide rail 101.

It is also conceivable to use the ground below the distance measurement camera 110 as the reference object, but since the ground is easily deformed due to the influence of the temperature or the like, it is difficult to distinguish whether or not the distance is changed due to the presence of the obstacle. Therefore, it is preferable to use a structure other than the ground as the reference object 111.

As illustrated in FIG. 15, the distance S from the distance measurement camera 110 to the reference object 111 is known. In addition, as illustrated in FIG. 16, it is preferable that the reference object 111 is formed in a slope shape with an upper portion as a vertex. Accordingly, it is possible to prevent the obstacle 112, such as a person, from riding on the reference object 111.

Basically, the functions of the distance measurement device according to the present embodiment are the same as the functions of the distance measurement device according to the second embodiment. In the present embodiment, the first measurement value L1 is a measurement value of a distance from the distance measurement camera 110 to the reference object 111. The second measurement value L2 is a measurement value of a distance from the distance measurement camera 110 to an obstacle 112 as the measurement object. The distance measurement processing according to the present embodiment is the same as the distance measurement processing according to the second embodiment illustrated in FIG. 13, except that one first measurement value L1 is used. Accordingly, it is possible to accurately measure the distance from the distance measurement camera 110 to the obstacle 112.

By using the distance measurement device according to the present embodiment, the distance from the distance measurement camera 110 to the obstacle 112 is always measured, and in a case where the obstacle 112 passes through the opening portion during the opening and closing of the shutter curtain 102, the opening and closing operation can be accurately and safely stopped.

It is assumed that a range of a measurement distance by the distance measurement device according to the present embodiment is about 0.5 m to 2 m, and the required measurement accuracy is about +30 mm. Since the shutter device is often used outdoors, there is a case where the shutter device may malfunction due to a measurement error of about +30 mm caused by factors such as a diurnal fluctuation of an air temperature and a seasonal fluctuation of an air temperature. By applying the distance measurement device according to the present embodiment, it is possible to prevent such a malfunction.

A hardware configuration of the processor in each of the above-described embodiments can be modified as follows.

The processor includes a CPU, a programmable logic device (PLD), a dedicated electric circuit, or a combination thereof. As is well known, the CPU is a general-purpose processor that executes software (that is, a program) to function as various processing units. The PLD is a processor of which the circuit configuration can be changed after manufacturing, and is, for example, a field programmable gate array (FPGA). The dedicated electric circuit is a processor having a circuit configuration specially designed for executing specific processing, such as an application specific integrated circuit (ASIC). Furthermore, the hardware structures of these various processors are more specifically electrical circuitry where circuit elements, such as semiconductor elements, are combined.

Two or more of the above-described embodiments and modification examples can be combined with each other as long as no contradiction occurs.

The technology of the present disclosure is not limited to the above-described embodiments and modification examples, and various configurations can be adopted without departing from the scope of the present disclosure. Furthermore, the technology of the present disclosure extends to a computer-readable storage medium that non-transitorily stores the program, in addition to the program.

The following technology can be ascertained by the above description.

[Supplementary Note 1]

A distance measurement device comprising:

a ToF type distance measurement camera that measures a distance to a measurement object and a distance to a reference object of which the distance is known; and a processor, wherein the processor calculates a correction coefficient on the basis of a first measurement value that is a measurement value of a distance from the distance measurement camera to the reference object obtained by the distance measurement camera and a known distance from the distance measurement camera to the reference object, and corrects a second measurement value that is a measurement value of a distance from the distance measurement camera to the measurement object obtained by the distance measurement camera or a calculation value calculated using the second measurement value.

[Supplementary Note 2]

The distance measurement device according to Supplementary Note 1, wherein a plurality of reference objects are provided, and the processor calculates the correction coefficient on the basis of an average value of a plurality of first measurement values that are measurement values of distances from the distance measurement camera to the plurality of reference objects obtained by the distance measurement camera, and known distances from the distance measurement camera to the plurality of reference objects.

[Supplementary Note 3]

The distance measurement device according to Supplementary Note 1 or 2, wherein the first measurement value is an average value of a plurality of measurement values obtained by measuring a distance from the distance measurement camera to the reference object a plurality of times by using the distance measurement camera.

[Supplementary Note 4]

The distance measurement device according to any one of Supplementary Notes 1 to 3, wherein the calculation value is a difference value between the first measurement value and the second measurement value.

[Supplementary Note 5]

The distance measurement device according to any one of Supplementary Notes 1 to 4, wherein the processor sets a value obtained by dividing the first measurement value by the known distance as the correction coefficient, and corrects the second measurement value or the calculation value by multiplying the second measurement value or the calculation value by the correction coefficient.

[Supplementary Note 6]

The distance measurement device according to any one of Supplementary Notes 1 to 5, wherein the processor updates the correction coefficient by acquiring the first measurement value for each constant time and calculating the correction coefficient.

[Supplementary Note 7]

The distance measurement device according to any one of Supplementary Notes 1 to 5, wherein the processor updates the correction coefficient by acquiring the first measurement value and calculating the correction coefficient at shorter intervals as an elapsed time from power supply turn-on of the distance measurement camera is shorter.

[Supplementary Note 8]

The distance measurement device according to any one of Supplementary Notes 1 to 7, further comprising:

a detection sensor that detects a position of the distance measurement camera with respect to the reference object, wherein the processor obtains the known distance by using a detection value detected by the detection sensor.

[Supplementary Note 9]

The distance measurement device according to any one of Supplementary Notes 1 to 8, wherein the reference object is an imaging stand, the measurement object is a subject disposed with respect to the imaging stand, the calculation value is a difference value between the first measurement value and the second measurement value, and the processor calculates a body thickness of the subject by multiplying the calculation value by the correction coefficient.

[Supplementary Note 10]

A radiography system comprising:

the distance measurement device according to Supplementary Note 9;

a radiation source that emits radiation toward the imaging stand; and a radiation image detector that is provided on the imaging stand and detects the radiation to generate a radiation image.

[Supplementary Note 11]

The radiography system according to Supplementary Note 10, wherein the distance measurement camera is attached to the radiation source.

What is claimed is:

1. A distance measurement device comprising:

a ToF type distance measurement camera that measures a distance to a measurement object and a distance to a reference object of which the distance is known;

a detection sensor that detects a position of the distance measurement camera with respect to the reference object; and a processor, wherein the processor:

obtains a known distance from the distance measurement camera to the reference object by using a detection value detected by the detection sensor, calculates a correction coefficient on the basis of a first measurement value that is a measurement value of a distance from the distance measurement camera to the reference object obtained by the distance measurement camera and the known distance, and corrects a second measurement value that is a measurement value of a distance from the distance measurement camera to the measurement object obtained by the distance measurement camera or a calculation value calculated using the second measurement value.

2. The distance measurement device according to claim 1, wherein a plurality of reference objects are provided, and the processor calculates the correction coefficient on the basis of an average value of a plurality of first measurement values that are measurement values of distances from the distance measurement camera to the plurality of reference objects obtained by the distance measurement camera, and known distances from the distance measurement camera to the plurality of reference objects.

3. The distance measurement device according to claim 1, wherein the first measurement value is an average value of a plurality of measurement values obtained by measuring a distance from the distance measurement camera to the reference object a plurality of times by using the distance measurement camera.

4. The distance measurement device according to claim 1, wherein the calculation value is a difference value between the first measurement value and the second measurement value.

5. The distance measurement device according to claim 1, wherein the processor sets a value obtained by dividing the first measurement value by the known distance as the correction coefficient, and corrects the second measurement value or the calculation value by multiplying the second measurement value or the calculation value by the correction coefficient.

6. The distance measurement device according to claim 1, wherein the processor updates the correction coefficient by acquiring the first measurement value for each constant time and calculating the correction coefficient.

7. The distance measurement device according to claim 1, wherein the processor updates the correction coefficient by acquiring the first measurement value and calculating the correction coefficient at shorter intervals as an elapsed time from power supply turn-on of the distance measurement camera is shorter.

8. The distance measurement device according to claim 1, wherein the reference object is an imaging stand, the measurement object is a subject disposed with respect to the imaging stand, the calculation value is a difference value between the first measurement value and the second measurement value, and the processor calculates a body thickness of the subject by multiplying the calculation value by the correction coefficient.

9. A radiography system comprising:

the distance measurement device according to claim 8;

a radiation source that emits radiation toward the imaging stand; and a radiation image detector that is provided on the imaging stand and detects the radiation to generate a radiation image.

10. The radiography system according to claim 9, wherein the distance measurement camera is attached to the radiation source.

11. An operation method of a distance measurement device provided with a ToF type distance measurement camera that measures a distance to a measurement object and a distance to a reference object of which the distance is known, and a detection sensor that detects a position of the distance measurement camera with respect to the reference object, wherein a processor executes processing including:

obtaining a known distance from the distance measurement camera to the reference object by using a detection value detected by the detection sensor, calculating a correction coefficient on the basis of a first measurement value that is a measurement value of a distance from the distance measurement camera to the reference object obtained by the distance measurement camera and the known distance, and correcting a second measurement value that is a measurement value of a distance from the distance measurement camera to the measurement object obtained by the distance measurement camera or a calculation value calculated using the second measurement value.

12. A non-transitory computer-readable storage medium storing an operation program for operating a distance measurement device including a ToF type distance measurement camera that measures a distance to a measurement object and a distance to a reference object of which the distance is known, and including a detection sensor that detects a position of the distance measurement camera with respect to the reference object, the operation program causing a processor to execute processing including:

obtaining a known distance from the distance measurement camera to the reference object by using a detection value detected by the detection sensor, calculating a correction coefficient on the basis of a first measurement value that is a measurement value of a distance from the distance measurement camera to the reference object obtained by the distance measurement camera and the known distance; and correcting a second measurement value that is a measurement value of a distance from the distance measurement camera to the measurement object obtained by the distance measurement camera or a calculation value calculated using the second measurement value.

* * * * *